United States Patent [19]
Edlund

[11] Patent Number: 5,139,541
[45] Date of Patent: Aug. 18, 1992

[54] HYDROGEN-PERMEABLE COMPOSITE METAL MEMBRANE

[75] Inventor: David J. Edlund, Bend, Oreg.

[73] Assignee: Bend Research, Inc., Bend, Oreg.

[21] Appl. No.: 734,177

[22] Filed: Jul. 22, 1991

Related U.S. Application Data

[63] Continuation-in-part of Ser. No. 566,092, Aug. 10, 1990.

[51] Int. Cl.⁵ .................... B01D 53/22; B01D 71/02
[52] U.S. Cl. .......................................... 55/16; 55/68; 55/158; 55/524
[58] Field of Search ............ 55/16, 68, 158, 524; 427/125, 126.3, 405, 419.2, 419.7; 428/609, 629, 636, 661, 662

[56] References Cited

U.S. PATENT DOCUMENTS 3,393,098  7/1968  Hartner et al. ................. 136/86
4,388,479  6/1983  Gryaznov et al. ............. 568/828

Primary Examiner—Robert Spitzer
Attorney, Agent, or Firm—Chernoff, Vilhauer, McClung & Stenzel

[57] ABSTRACT

Composite metal membranes are disclosed that contain an intermetallic diffusion barrier separating a hydrogen-permeable base metal and a hydrogen-permeable coating metal. The barrier is a thermally stable inorganic proton conductor.

15 Claims, 1 Drawing Sheet

: =

HYDROGEN-PERMEABLE COMPOSITE METAL MEMBRANE

The government has rights in this invention pursuant to Grant No. ISI-8722212 awarded by the National Science Foundation.

This is a continuation-in-part of application Ser. No. 566,092 filed Aug. 10, 1990.

BACKGROUND OF THE INVENTION

Metal membranes that are selectively permeable to hydrogen are known. See, for example, U.S. Pat. No. 4,388,479 and 3,393,098, both of which disclose Group V and VIII alloy membranes such as palladium alloy catalytic membranes. The prohibitively high cost of palladium has lead to efforts to fabricate composite hydrogen-permeable metal membranes by coating certain transition metal alloy base metals with palladium or palladium alloys. See, for example, U.S. Pat. Nos. 4,468,235 and 3,350,846. The coating on such base metals imparts chemical resistance to the base metal and in some cases increases the rate of adsorption of hydrogen onto the metal membrane surface. However, such coated metal membranes have an inherent shortcoming in that, under the elevated temperature conditions of use or fabrication by diffusion welding, the coating metal tends to diffuse into the base metal, thereby destroying the benefits available from such composite metal membranes. U.S. Pat. No. 4,496,373 discloses a nonporous hydrogen-permeable composite metal membrane that addresses this intermetallic diffusion problem for a base metal alloy of a specific composition coated with a palladium alloy of specific composition. However, the composition of the palladium alloy coating and the base metal alloy are narrowly defined so as to favor partitioning of the palladium into the coating alloy as opposed to the base metal alloy. Consequently, this approach is not general in nature, requires strict control over alloy composition, and allows for little variation in selection of metals for membrane fabrication.

These and other shortcomings of prior art hydrogen-permeable composite metal membranes are overcome by the present invention, which is summarized and described in detail below.

SUMMARY OF THE INVENTION

The present invention provides a novel nonporous composite hydrogen-permeable metal membrane and method of using the same for the selective separation of hydrogen. The essential structure of the membrane comprises a hydrogen-permeable base metal and a hydrogen-permeable coating metal separated by a barrier which prevents intermetallic diffusion between said base metal and said coating metal at a temperature of at least 500° C., said barrier comprising an inorganic proton conductor other than pure metal or a pure metal alloy. Such metal membranes have utility not only in separating hydrogen from other gases, but in a number of other reactions where hydrogen is either a reactant or a reaction product.

DETAILED DESCRIPTION OF THE INVENTION

The base metal of the metal membrane of the present invention is selected from hydrogen-permeable transition metals from Groups IIIB, IVB, VB, VIIB and VIIIB of the periodic table and alloys containing $\geq 20$ wt% of said metals, and may be from 25 to 250 microns in thickness.

The coating metal is a hydrogen-permeable transition metal that is chemically and physically stable at temperatures of at least 500° C., is preferably selected from the transition metals of Groups VIIB and VIIIB of the periodic table, most preferably Fe, Mn, Ni, Pd, Pt, Ru and alloys containing $\geq 20$ wt% of said metals, and preferably from 0.01 to 1.0 micron in thickness.

The intermetallic diffusion barrier is a thermally stable inorganic proton conductor other than pure metal or a pure metal alloy. "Proton conductor" refers not only to $H^+$ ion-conducting materials, but broadly to any material that shows complex ion motion at high temperatures, such as do the oxides and sulfides of molybdenum, silicon, tungsten and vanadium; doped $SrCeO_3$ ($SrCe_{1-x}M_xO_{3-\alpha}$ where x is from 0.05 to 0.10, $\alpha$ is a variable determined by the oxidation state of M, and M is a metal selected from Dy, In, Mg, Nd, Sm, Y, Yb, and Zn; see Iwahara et al., "Solid State Ionics", pp. 359–363 (1981)); $Zr(HPO_4)_2$; the glasses $PbO-SiO_2$, $BaO-SiO_2$, and $CaO-SiO_2$; the $M_3H(TO_4)_2$ family of crystals (where M is $NH_4^+$, K, Rb or Cs and T is S or Se); yttrium-substituted oxyhydroxyapatite; $\beta$-Ca($PO_3$)$_2$; and $RbHSeO_4$.

In a most preferred form, the barrier is selected from the group consisting essentially of oxides of molybdenum, silicon, tungsten and vanadium, and sulfides of molybdenum, tungsten and vanadium, and is from 0.1 to 25 microns in thickness.

Figure 1:
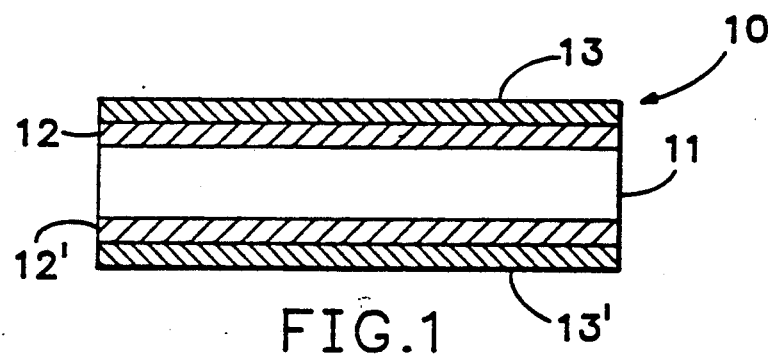
FIG. 1 is a schematic cross-sectional view of an exemplary composite membrane of the present invention.

Referring to FIG. 1, there is shown a preferred exemplary embodiment of a composite metal membrane 10 comprising a base metal layer 11, two intermetallic diffusion barrier layers 12 and 12' and two coating layers 13 and 13'. Although two layers 12 and 12' and 13 and 13' are shown, composite metal membranes having only single layers 12 and 13 also comprise useful embodiments of the present invention.

Figure 2:
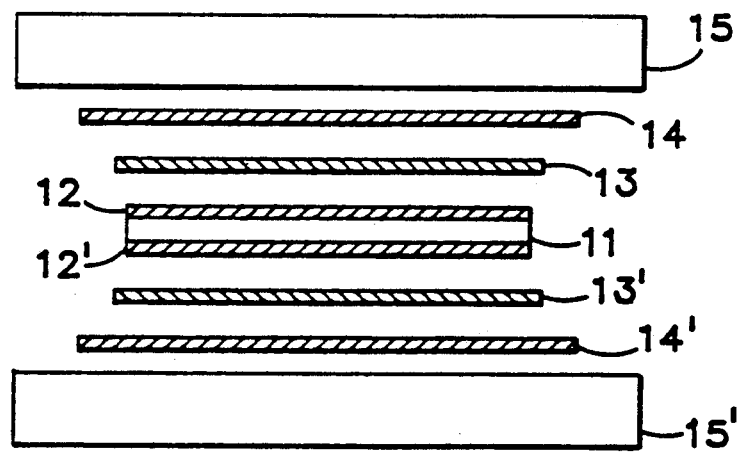
FIG. 2 is a schematic cross-sectional exploded view of an exemplary method of making the composite membrane of the present invention.

Fabrication of the composite metal membranes of the present invention is preferably by a temperature/pressure lamination of the three components. FIG. 2 schematically illustrates such a fabrication technique. In FIG. 2, there is shown an exploded cross-sectional view of the composite metal membrane of FIG. 1 prior to lamination, and wherein like numerals correspond to the same elements. In FIG. 2 there are shown graphite gaskets 14 and 14' and stainless steel press plates 15 and 15'. The graphite gaskets 14 and 14' seal the membrane against exposure to air during the lamination in order to protect against oxidation. The intermetallic diffusion barrier is preferably first applied chemically to the base metal by deposition thereon of an inorganic oxide or sulfide layer. In the case of oxides, the base metal may be coated by spraying, spinning or dipping with a solution of a precursor to the oxide, such as $SiCl_4$ (or $Si(O-Me)_4$ with a catalytic amount of concentrated HCl), $WCl_6$ or $MoCl_5$, which then hydrolyzes to form the oxide layer. In the case of metal sulfide layers, the base metal may be simply exposed to a sulfide gas, such as hydrogen sulfide, at elevated pressure and temperature for a short time, such as 5 to 15 minutes. Alternatively, the base metal may be coated by spraying, spinning, or dipping with a solution of a precursor to the sulfide, such as $WCl_6$, $MoCl_5$ or $VCl_3$, which may then be reacted with hydrogen sulfide to form the sulfide layer. Yet another method for applying the oxide or sulfide layer is by vapor deposition of the desired oxide or sulfide onto the base metal.

The composite membrane of the present invention is selectively permeable to hydrogen gas and may be used in virtually any reaction where hydrogen is either a reactant or a product and is advantageously isolated, reflected in the two reaction schemes $A + H_2 \rightarrow B$ $A \rightarrow B + H_2$.

A prime example of such a class of reactions is the separation of hydrogen from other gases such as nitrogen, carbon monoxide, carbon dioxide, methane, ethane, ethylene, propane, propylene, steam or ammonia by methods known in the art, the essential features of which comprise contacting a feed gas containing hydrogen and other gases at temperatures generally exceeding 500° C., allowing the selective permeation of hydrogen through the composite membrane, and collecting the permeated hydrogen.

Other examples of the broad class of reactions include the decomposition of hydrogen sulfide, the synthesis of ammonia, the synthesis of synthetic fuels such as by the Fischer-Tropsch synthesis, steam reforming of hydrocarbons, dehydrogenation of hydrocarbons to produce unsaturated hydrocarbons such as olefins and aromatics, and the water-gas ($CO_2$)-shift reaction.

EXAMPLE 1

A Ni/$SiO_2$/V composite metal membrane was made using the following procedure. A vanadium disc, 5 cm in diameter and 152 microns thick, served as the base metal, providing good mechanical properties to the composite membrane. Six-micron-thick nickel foil served as the coating material, providing chemical inertness to the composite membrane. A thin layer of $SiO_2$ between the vanadium and nickel prevented diffusion of the nickel coating into the vanadium base metal.

To fabricate the composite metal membrane, a thin layer of $SiO_2$ was deposited on both sides of the vanadium by dip-coating the vanadium disc with a 1M solution of $SiCl_4$ in methylene chloride at room temperature. As the methylene chloride solvent evaporated, the $SiCl_4$ rapidly hydrolyzed in the presence of atmospheric moisture to yield a film of $SiO_2$ approximately 25 microns thick. Good adhesion between the $SiO_2$ layer and the vanadium was observed. Next, the $SiO_2$-coated vanadium was laminated with the nickel foil at 700° C. under 20,000 pounds of pressure for 4 hours as shown schematically in FIG. 2 to produce the composite membrane. The composite membrane so prepared was flexible, and showed no sign of delamination when bent.

Hydrogen flux through the composite membrane was measured at 700° C. using a hydrogen gas feed stream at 100 psig (690 kPa), the permeated hydrogen being at ambient pressure. For comparison, the hydrogen flux through a control membrane made by laminating the same thickness of nickel foil directly to the same thickness of vanadium without the use of an intervening $SiO_2$ layer was measured under identical conditions. The results are given in the table below after 30 hours and 50 hours of operation. For this composite membrane, the layer that has the greatest resistance to hydrogen permeation (i.e., the layer that has the lowest hydrogen permeability) is the thin nickel coating (the limiting hydrogen flux through a nickel membrane 5 cm in diameter and 25 microns thick is 0.9 $m^3/m^2$.hr). Since the observed rate of hydrogen permeation through the composite membrane cannot exceed the rate of permeation through each chemically distinct layer of the membrane, the nickel coating of the Ni/$SiO_2$/V membrane limits the overall hydrogen flux.

| Membrane | $H_2$ Flux* (30 hrs) | $H_2$ Flux* (50 hrs) |
|---|---|---|
| Ni/$SiO_2$/V | 0.9 | 0.6 |
| Ni/V | 0.15 | 0.006 |

*Average $m^3/m^2 \cdot hr$

As this Example shows, the Ni/$SiO_2$/V composite metal membrane shows higher flux and longer lifetime than the Ni/V control membrane indicating that the $SiO_2$ metal diffusion barrier is effective at preventing diffusion of the Ni coating into the vanadium base metal. There is no such barrier in the Ni/V control membrane to prevent diffusion of Ni into the vanadium and subsequent deterioration of the Ni coating. When the protective Ni coating deteriorates sufficiently, the vanadium base metal is exposed to feedstream impurities ($N_2$, $O_2$, and possibly other gases) that react with the vanadium metal, resulting in a decrease in the hydrogen permeability of the vanadium, which is manifested as a decrease in hydrogen flux through the Ni/V control membrane.

EXAMPLE 2

A NiCu/$SiO_2$/V composite metal membrane was made as follows. A vanadium disc, 5 cm in diameter and 152 microns thick, served as the base metal. NiCu foil (20 wt% Ni, 80 wt% Cu) 31 microns thick (made by laminating a 6-micron Ni foil to a 25-micron Cu foil) served as the coating material, providing chemical inertness to the composite membrane. A thin layer of $SiO_2$ between the vanadium and the NiCu coating served as the intermetallic diffusion barrier. A 25-micron-thick layer of $SiO_2$ was deposited on both sides of the vanadium by spin coating the vanadium with a 1M solution of $Si(OMe)_4$ in methanol containing a catalytic amount of concentrated HCl. The $SiO_2$-coated vanadium was laminated with the NiCu foil in substantially the same manner as in Example 1 with substantially the same results.

Hydrogen flux through the so-fabricated composite membrane was measured in the same manner as in Example 1. For comparison, the hydrogen flux through a control membrane made by laminating the same thickness of NiCu foil directly to the same thickness of vanadium without the use of an intervening $SiO_2$ layer was measured under identical conditions. The results are given in the table below after 72 hours of operation.

| Membrane | $H_2$ Flux* |
|---|---|
| NiCu/$SiO_2$/V | 2.4 |
| NiCu/V | 0.06 |

*Average $m^3/m^2 \cdot hr$.

As is apparent, the composite metal membrane showed higher flux and longer lifetime than both the NiCu/V control membrane of this Example and the Ni/V control membrane of Example 1.

EXAMPLE 3

A Ni/V-sulfide/V composite metal membrane was made as follows. A vanadium disc, 5 cm in diameter and 152 microns thick, served as the base metal, while a 6 micron-thick Ni foil served as the coating material. A thin layer of vanadium sulfide served as the intermetallic diffusion barrier, which was deposited on both sides of the vanadium by exposing the vanadium disc to 30 psig $H_2S$ at 700° C. for 10 minutes. Good adhesion between the vanadium sulfide layer and the vanadium was observed. The vanadium sulfide-coated vanadium was then laminated with the Ni foil at 700° C. under 20,000 pounds of pressure for 4 hours.

The hydrogen flux through the composite membrane was measured in the same manner as in Example 1 and compared with the hydrogen flux through a control membrane made by laminating the same thickness of Ni foil directly to the same thickness of vanadium under identical conditions without the use of an intervening sulfided-vanadium layer. The results after 50 hours of operation are given in the table below. As is apparent, the composite membrane showed higher flux and longer lifetime than the Ni/V control membrane. The flux through the composite membrane of this Example was less than that of Example 1 due to the lower hydrogen permeability of the vanadium sulfide layer relative to the $SiO_2$ layer.

| Membrane | $H_2$ Flux* |
|---|---|
| Ni/V-sulfide/V | 0.046 |
| Ni/V | 0.004 |

*Average $m^3/m^2 \cdot hr$

EXAMPLE 4

A Pd/SiO$_2$/V composite metal membrane was made as follows. A vanadium disc, 5 cm in diameter and 30 microns thick, served as the base metal, while a 25-micron-thick palladium foil served as the coating material. A thin layer of $SiO_2$ served as the intermetallic diffusion barrier. The $SiO_2$ layer was deposited on one surface of each of two 5-cm-diameter pieces of Pd foil by first placing a thin film of methanol containing a catalytic amount of HCl on the surfaces of the Pd, then, before the methanol/HCl evaporated, adding Si(OMe)$_4$ dropwise until each of the Pd surfaces was entirely covered; this yielded a 25-micron-thick $SiO_2$ layer by hydrolysis of the Si(OMe)$_4$ due to reaction with atmospheric moisture. The two pieces of $SiO_2$-coated Pd foil were placed $SiO_2$ layer down on both sides of the vanadium disc. The entire assembly was then placed directly in a permeation test cell and laminated in situ during permeation testing at 700° C. using the gas feed-pressure of 100 psi (690 kPa) to achieve lamination. The average hydrogen flux through the composite membrane was measured for nearly six hours and stabilized after about two hours at 25.3 $m^3/m^2$.hr. This high flux is a result of using palladium as the coating metal, rather than nickel or nickel/copper alloy, which has a greater permeability to hydrogen than do nickel or nickel/copper alloys.

For comparison, the hydrogen flux through a control membrane made by laminating the same thickness of palladium foil directly to the same thickness of vanadium foil without the use of an intervening $SiO_2$ layer was measured under identical conditions. The flux through this control membrane decreased steadily from the initial value of 19 $m^3/m^2$. hr to 14 $m^3/m^2$.hr after 6 hours, then to 0.91 $m^3/m^2$. hr after 50 hours operation. As is apparent, the composite membrane exhibited higher flux and longer lifetime than the Pd/V control membrane.

EXAMPLE 5

To demonstrate high permeability of the $SiO_2$ layer, a Pd/SiO$_2$/Pd composite metal membrane was made. Palladium served as the coating metal and the base metal was omitted. Palladium foil, 5 cm in diameter and 25 microns thick, was coated on one side with a thin layer of $SiO_2$ as in Example 4. Another piece of palladium foil of the same dimensions was then placed over the $SiO_2$-coated palladium so that the $SiO_2$ layer was between the two. The assembly was then placed in a permeation test cell and laminated in situ as in Example 5. The average hydrogen flux through the composite membrane was measured and observed to stabilize at 31 $m^3/m^2$.hr.

EXAMPLE 6

To demonstrate the high permeability of a $WO_3$ layer for use as a metal-diffusion barrier, a Pd/WO$_3$/Pd composite metal membrane was made. Palladium served as the coating metal and the base metal was omitted. Palladium foil, 5 cm in diameter and 25 microns thick, was coated on one side with a thin layer of $WO_3$ by applying to one surface a solution of $WCl_6$ in a mixture comprising about 94% methylene chloride, about 5% acetonitrile, and about 1% Si(OMe)$_4$. The $WCl_6$ rapidly hydrolyzed in the presence of atmospheric moisture to yield a thin film of $WO_3$. Another piece of palladium foil of the same dimensions was then placed over the $WO_3$-coated palladium so that the $WO_3$ layer was between two layers of palladium. The assembly was then placed in a permeation test cell and laminated in situ as in Example 4. The average hydrogen flux through the composite membrane was measured and observed to stabilize at 42 $m^3/m^2$.hr.

EXAMPLE 7

To demonstrate the high permeability of a $MoO_3$ layer for use as a metal-diffusion barrier, a Pd/MoO$_3$/Pd composite metal membrane similar to that of Examples 5 and 6 was made as follows. Palladium foil, 5 cm in diameter and 25 microns thick, was coated on one side with a thin layer of $MoO_3$ by applying to one surface a solution of $MoCl_5$ in the same solvent mixture as in Example 6. The $MoCl_5$ rapidly hydrolyzed in the presence of atmospheric moisture to yield a thin film of $MoO_3$. Another piece of palladium foil of the same dimensions was then placed over the $MoO_3$-coated palladium so that the $MoO_3$ layer was between the two pieces of palladium. The assembly was then placed in a permeation test cell and laminated in situ as in Example 4. The average hydrogen flux through the composite membrane was measured and was observed to stabilize at 67 $m^3/m^2$.hr.

EXAMPLE 8

A Ni/MoO$_3$/Cu composite metal membrane was made as follows. A copper disc, 5 cm in diameter and 250 microns thick, served as the base metal, while a 25-micron-thick nickel foil served as the coating material. A thin layer of $MoO_3$ served as the metal diffusion barrier, and was deposited on one surface of each of two pieces of 5-cm-diameter nickel foil as in Example 7. The two pieces of $MoO_3$-coated nickel foil were placed $MoO_3$-side down on both sides of the copper foil. The entire assembly was then placed directly in a permeation test cell and laminated in situ during permeation testing as in Example 4. Average hydrogen flux through the composite membrane was measured and observed to stabilize at 0.37 $m^3/m^2.hr$. This flux is identical to that through a copper membrane (250 microns thick, 5 cm diameter) under the same conditions of temperature and hydrogen pressure. Therefore, as expected, the copper base-metal layer is the limiting factor in the overall flux through this composite membrane.

What is claimed is:

1. A nonporous composite metal membrane comprising a hydrogen-permeable base metal and a hydrogen-permeable coating metal characterized in that said base metal and said coating metal are separated by a barrier which prevents intermetallic diffusion between said base metal and said coating metal at a temperature of at least 500° C., said barrier comprising an inorganic proton conductor other than pure metal or a pure metal alloy.

2. The metal membrane of claim 1 wherein said barrier is selected from the group consisting essentially of oxides of molybdenum, silicon, tungsten and vanadium, and sulfides of molybdenum, tungsten and vanadium.

3. The metal membrane of claim 1 wherein said base metal is selected from hydrogen-permeable transition metals from Groups IIIB, IVB, VB, VIIB and VIIIB of the periodic table and alloys containing $\geq 20$ wt% of said metals.

4. The metal membrane of claim 1 wherein said coating metal is selected from a hydrogen-permeable transition metal and alloy thereof, said coating metal being chemically and physically stable at temperatures of at least 500° C.

5. The metal membrane of claim 4 wherein said coating metal is selected from the group consisting essentially of the transition metals from Groups VIIB and VIIIB of the periodic table, and alloys containing $\geq 20$ wt% of said metals.

6. The metal membrane of claim 5 wherein said coating metal is selected from the group consisting essentially of Fe, Mn, Ni, Pd, Pt and Ru.

7. The metal membrane of claim 1 wherein said barrier is molybdenum oxide.

8. The metal membrane of claim 1 wherein said barrier is silicon dioxide.

9. The metal membrane of claim 1 wherein said barrier is tungsten oxide.

10. The metal membrane of claim 1 wherein said barrier is vanadium oxide.

11. The metal membrane of claim 1 wherein said barrier is vanadium sulfide.

12. The metal membrane of claim 1 wherein said base metal is vanadium and said coating metal is an alloy comprising 20 wt% nickel and 80 wt% copper.

13. The metal membrane of claim 1 wherein said base metal is vanadium and said coating metal is palladium.

14. The metal membrane of claim 1 wherein said base metal is vanadium and said coating metal is nickel.

15. A method for separating hydrogen from other gases comprising contacting a gaseous feed stream containing hydrogen at a temperature of at least 500° C. with the metal membrane of claim 1 or 2 and separating hydrogen that permeates through said metal membrane.

* * * * *

UNITED STATES PATENT AND TRADEMARK OFFICE
CERTIFICATE OF CORRECTION

PATENT NO. : 5,139,541

DATED : August 18, 1992

INVENTOR(S) : David J. Edlund

It is certified that error appears in the above-identified patent and that said Letters Patent is hereby corrected as shown below:

Col. 4, line 8   Change "$m^2.hr.$" to --$m^2 \cdot hr.$--

Col. 5, line 62  Change "$m^2.hr.$" to --$m^2 \cdot hr.$--

Col. 6, line 4   Change "$m^2.hr.$" to --$m^2 \cdot hr.$-- (both occurrences)

Col. 6, line 5   Change "$m^2.hr.$" to --$m^2 \cdot hr.$--

Col. 6, line 24  Change "$m^2.hr.$" to --$m^2 \cdot hr.$--

Col. 6, line 44  Change "$m^2.hr.$" to --$m^2 \cdot hr.$--

Col. 6, line 63  Change "$m^2.hr.$" to --$m^2 \cdot hr.$--

Col. 7, line 11  Change "$m^2.hr.$" to --$m^2 \cdot hr.$--

Signed and Sealed this

Twelfth Day of October, 1993

Attest:

BRUCE LEHMAN

Attesting Officer

Commissioner of Patents and Trademarks